United States Patent [19]

Stein

[11] 4,388,236
[45] Jun. 14, 1983

[54] ENKEPHALIN-LIKE COMPOUNDS IN BOVINE ADRENAL MEDULLA

[75] Inventor: Stanley Stein, Bloomfield, N.J.

[73] Assignee: Hoffmann-La Roche Inc., Nutley, N.J.

[21] Appl. No.: 374,825

[22] Filed: May 4, 1982

Related U.S. Application Data

[60] Continuation-in-part of Ser. No. 253,984, Apr. 13, 1981, abandoned, which is a continuation-in-part of Ser. No. 157,137, Jun. 6, 1980, which is a division of Ser. No. 70,960, Aug. 29, 1979.

[51] Int. Cl.³ ............................................. C07C 103/52
[52] U.S. Cl. ............................................. 260/112.5 R
[58] Field of Search ................................. 260/112.5 R

[56] References Cited

U.S. PATENT DOCUMENTS 4,073,885  2/1978  Pert et al. ............................ 424/177

Primary Examiner—Delbert R. Phillips
Attorney, Agent, or Firm—Jon S. Saxe; George M. Gould; Peter R. Shearer

[57] ABSTRACT

Enkephalin-like compounds having opiate agonist activity and useful as analgesic agents are extracted from bovine adrenal glands.

7 Claims, No Drawings

ENKEPHALIN-LIKE COMPOUNDS IN BOVINE ADRENAL MEDULLA

CROSS REFERENCE TO RELATED APPLICATIONS

This application is a continuation-in-part of U.S. patent application Ser. No. 253,984, filed Apr. 13, 1981, now abandoned, which is a continuation-in-part of U.S. patent application Ser. No. 157,137, filed June 6, 1980, which is a divisional of U.S. patent application Ser. No. 70,960, filed Aug. 29, 1979.

BACKGROUND OF THE INVENTION

Compounds having opiate activity and useful as analgesic agents have been isolated from extracts of animal tissue and their amino acid sequences determined, in particularly the pentapeptides methionine enkephalin (Met-Ek) and leucine enkephalin (Leu-Ek) [Hughes, J. et al., Nature 258, 577 (1975)]. Both Met-Ek and Leu-Ek from mammalian brain have been shown to produce a weak and short term analgesia following intracerebraventricular or intravenous administration to mice [Buscher, H. H., et al., Nature 261, 423 (1976)] and rats [Belluggi, J. D., et al., Nature 260, 625, (1976)], and have been assumed to arise biologically from the larger enkephalin containing peptide, β-endorphin.

Immunocytochemical observations of the adrenal medulla [Schultzberg, M. et al., Neuroscience 3, 1169 (1978)] have shown the presence of relatively large amounts of material immunoreactive with enkephalin peptides. Other reports of enkephalin peptides isolated and characterized from bovine adrenal medualla have been made, i.e. Lewis, R. V., et al., in Biochem, Biophys. Res. Commun. 89, 822, (1979); in Neural Peptides and Neural Communication (Costa, E., and Trabucchi, M., eds) pp 167–179, Raven Press, New York; and in Science 208, 1459 (1980); Kumura, S., et al., Proc. Nat. Acad. Sci. U.S.A. 77, 1681–1685 (1980).

Kensaku, et al., Biochem. Biophys. Res. Comm. 95, 1482–1488 (1980) reported the isolation from bovine adrenal medulla of a dodecapeptide having the following sequence of amino acids:

```
 1                   5
Tyr—Gly—Gly—Phe—Met—Arg—Arg—
                              10
             Val—Gly—Arg—Pro—Glu
```

SUMMARY OF THE INVENTION

The present invention relates to peptidic compounds that are endogenous in mammalian adrenal glands and that are enkephalin-like in that such compounds are structurally related to Met-Ek and Leu-Ek in that the compounds of the invention contain a Met-Ek and/or Leu-Ek structure within their peptide sequence, and have opiate agonist activity and are useful as analgesic agents. The compounds of this invention are distinctly different from β-endorphin and have been purified to be essentially free of other endogenous peptides.

DETAILED DESCRIPTION OF THE INVENTION

The present invention relates to the isolation, purification and characterization of endogenous polypeptides containing enkephalin-sequences. The polypeptides are obtained from bovine adrenal glands and have properties customarily associated with enkephalins in that these polypeptides contain a Met-Ek and/or Leu-Ek amino acid sequence. As a result of containing a Met-Ek and/or Leu-Ek amino acid sequence, the polypeptides of this invention are opiates useful as analgesic agents.

In particularly the present invention relates to peptidic compounds endogenous in mammalian adrenal glands, essentially free of other endogenous peptides and having the following amino acid sequences:

```
                         Peptide B
 1                 5                    10
Phe—Ala—Glu—Pro—Leu—Pro—Ser—Glu—Glu—Glu—Gly 15                  20
   Glu—Ser—Tyr—Ser—Lys—Glu—Val—Pro—Glu—Met—Glu—

25                30
                     Lys—Arg—Tyr—Gly—Gly—Phe—Met—Arg—Phe

Peptide E
 1                 5                    10
Tyr—Gly—Gly—Phe—Met—Arg—Arg—Val—Gly—Arg—Pro—Glu—Trp—Trp—

15                  20                25
       Met—Asp—Tyr—Gln—Lys—Arg—Tyr—Gly—Gly—Phe—Leu

Peptide F
 1                 5                    10
Tyr—Gly—Gly—Phe—Met—Lys—Lys—Met—Asp—Glu—Leu—Tyr—Pro—Leu—

15               20                 25
Glu—Val—Glu—Glu—Glu—Ala—Asn—Gly—Gly—Glu—Val—Leu—Gly—Lys—

30              34
                            22 Arg—Tyr—Gly—Gly—Phe—Met

Peptide I
              1                5                   10
          Ser—Pro—His—Leu—Glu—Asp—Glu—Thr—Lys—Glu—Leu—Gln—Lys—Arg—
```

-continued

```
         15              20              25
Tyr—Gly—Gly—Phe—Met—Arg—Arg—Val—Gly—Arg—Pro—Glu—Trp—Trp—

30              35                  39
           Met—Asp—Tyr—Gln—Lys—Arg—Tyr—Gly—Gly—Phe—Leu
```

Peptide V-16

Tyr—Gly—Gly—Phe—Met—Arg—Phe as well as to other peptidic compounds endogenous in mammalian adrenal glands, essentially free of other endogenous peptides and having molecular weights of approximately 14,000, 11,000 and 8,000 daltons and designated 14 kilodalton (14 k), 11 kilodalton (11 k) and 8 kilodalton (8 k), respectively.

The 14 k, 11 k and 8 k peptidic compounds of this invention have, respectively, the following amino acid sequence:

Peptide 14 k

```
               5                     10
Glu—Cys—Ser—Gln—Asp—Cys—Ala—Thr—Cys—Ser—Tyr—

15                    20
Arg—Leu—Ala—Arg—Pro—Thr—Asp—Leu—Asp—Pro—Leu—

25                    30
Ala—Cys—Thr—Leu—Glu—Cys—Glu—Gly—Lys—Leu—Pro—

35                    40
Ser—Leu—Arg—Thr—Trp—Glu—Thr—Cys—Lys—Glu—Leu—

45                 50                  55
Leu—Gln—Leu—Thr—Lys—Leu—Glu—Leu—Pro—Pro—Asp—

60                     65
Ala—Thr—Ser—Ala—Leu—Ser—Lys—Gln—Glu—Glu—Ser—

70                  75
His—Leu—Leu—Ala—Lys—Lys—Tyr—Gly—Gly—Phe—Met—

80                    85
Lys—Arg—Tyr—Gly—Gly—Phe—Met—Lys—Lys—Met—Asp—

90                 95
Glu—Leu—Tyr—Pro—Leu—Glu—Val—Glu—Glu—Glu—Ala—

100              110                  115
Asn—Gly—Gly—Glu—Val—Leu—Gly—Lys—Arg—Tyr—Gly—

Gly—Phe—Met
```

Peptide 11 k

```
               5                     10
Asp—Ala—Glu—Glu—Asp—Asp—Gly—Leu—Gly—Asn—Ser—

15                    20
Ser—Asn—Leu—Leu—Lys—Glu—Leu—Leu—Gly—Ala—Gly—

25                 30                35
Asp—Gln—Arg—Glu—Gly—Ser—Leu—His—Gln—Glu—Gly—

35                 40
Ser—Asp—Ala—Glu—Asp—Val—Ser—Lys—Arg—Tyr—Gly—

45                 50
           Gly—Phe—Met—Arg—Gly—Leu
```

Peptide 8 k

```
               5
Glu—Cys—Ser—Gln—Asp—Cys—Ala—Thr—Cys—Ser—Tyr—

10                  15                    20
Arg—Leu—Ala—Arg—Pro—Thr—Asp—Leu—Asp—Pro—Leu—

25                    30
Ala—Cys—Thr—Leu—Glu—Cys—Glu—Gly—Lys—Leu—Pro—

35                      40
Ser—Leu—Arg—Thr—Trp—Glu—Thr—Cys—Lys—Glu—Leu—

45                      50
Leu—Gln—Leu—Thr—Lys—Leu—Glu—Leu—Pro—Pro—Asp—

55                      60
Ala—Thr—Ser—Ala—Leu—Ser—Lys—Gln—Glu—Glu—Ser—

65                      70                   75
His—Leu—Leu—Ala—Lys—Lys—Tyr—Gly—Gly—Phe—Met
```

The peptidic compounds of this invention are further characterized as follows:

(a) each exhibits opiate agonist activity which is enhanced upon trypsin digestion;

(b) each is immunoreactive with N-terminal specific enkephalin antibody;

(c) each provides positive response in enkephalin radioreceptor assay;

(d) each is slightly immunoreactive with C-terminal specific enkephalin antibody;

(e) each has substantial enhancement of (b), (c), and (d) activities after digestion with trypsin; and (f) each has an amino acid composition as disclosed hereafter in Table II.

All the peptidic compounds of this invention are enkephalin-containing polypeptides which are endogenous in bovine adrenal medulla and may be obtained and purified in accordance with the processes which follow.

Extracts of bovine adrenal medulla (BAM) or chromaffin granules (CG) therefrom were obtained by conventional methods known in the art and were purified using gel filtration, high pressure liquid chromatography (HPLC) and fluorometric detection by method of Bohlen, P. et al., Anal. Biochem. 67, 437 (1975). The foregoing purification processes provide high molecular weight proteins that can be cleaved with trypsin to yield peptides with opioid activity in both radioreceptor assays as by the method of Gerber, L. D. et al., Brain Res. 151, 117-126 (1978) and radioimmunoassays. In addition to these high molecular weight proteins there are a number of smaller peptides some of which are active in their native form while others are active only after tryptic digestion. Several of these peptides and precursors were isolated and purified to homogeneity.

More particularly the extracts from BAM or CK were purified in accordance with the following scheme:

---

Purification Scheme for Enkephalin-Containing Polypeptides from BAM or CK

---

Acid Extracts from BAM or CG

| Sephadex G-100 or Sephadex G-75

Fractions with Enkephalin-Containing Polypeptides

| Purification Scheme for Enkephalin-Containing Polypeptides from BAM or CK |
| --- |
| Ultrasphere Octyl (C8)    Lichrosorb RP-18 (C18)    Spherisorb CN (CN) |
| Fractions with Enkephalin-Containing Polypeptides |

In a typical preparatory procedure for obtaining purified enkephalin-containing polypeptides of this invention, BAM or CG is prepared from bovine adrenal glands by conventional procedures such as by the procedure of Smith and Winkler [Biochem. J. 103, 480–482, (1967)]. The resulting isolated BAM or CG is homogenized (10:1 volume per weight) in a solution of 1 M acetic acid, 20 mM HCl and 0.1% 2-mercaptoethanol containing 1 µg/ml each of phenylmethanesulfonyl fluoride and pepstatin. The procedure employed for acid extraction of BAM or CG is that of Lewis et al., [PNAS, 75, 4021–4023 (1978)] which provides thereby an acid extract of BAM or CG.

The initial separation of the enkephalin-containing polypeptides in the acid extract is by gel filtration on Sephadex G-100 in accordance with the method of Lewis et al., Biochem. Biophys. Res. Comm. 89, 822–829 (1979).

Chromatography of extracts of BAM by gel filtration on Sephadex G-100 gives five peaks of radioreceptor active material. Extracts of CG from the bovine adrenal medulla were also subjected to the same chromatography on Sephadex G-100 by procedures conventionally used in the art. The same five peaks of activity are again observed and are designated peaks I to V.

These peaks, i.e. I–V, whether from extracts of BAM or CG, represent proteineous substances having molecular weights of approximately 20–24,000 for peak I; 10–15,000 for peak II; 7–10,000 for peak III; 3–5,000 for peak IV; and about 1,000 for peak V.

Opioid activities for peaks I–V were quantitatively determined by conventional means in radioreceptor assays before (Native) and after trypsin digestion of each of the peaks from BAM and CG sources. The results (Table I) show that the amounts of activity in peaks II, III, and IV relative to each other are similar from both sources. The amount of peak I relative to the other peaks was found to be more than 3-fold higher in the whole medulla than in the granules. Since peaks I, II, III and IV all showed considerably greater activity in the radioreceptor assay when predigested with trypsin, active peptide sequence must be contained within a larger peptide.

TABLE 1

| Radioreceptor Assay of Peaks From Sephadex G-100 | | |
| --- | --- | --- |
| Peak | Trypsin Digested | Native |
| Adrenal Medulla[1] | | |
| I | 6.9 | 0.6 |
| II | 12.5 | <0.05 |
| III | 10.9 | 1.9 |
| IV | 5.1 | 2.2 |
| V | 12.0 | 12.4 |
| Chromaffin Granules[1] | | |
| I | 0.8 | 0.2 |
| II | 4.7 | 0.7 |
| III | 4.4 | 2.4 |
| IV | 1.7 | 0.6 |
| V | 4.8 | 5.0 |

[1]These values are for 10 g wet weight of bovine adrenal medulla without correction for recovery as nmoles/peak.

Aliquots of the five peaks produced by Sephadex G-100 gel filtration from BAM and CG were assayed with or without digestion with trypsin. Tryptic peptides derived from peaks I–IV interacted well with the N-terminal specific enkephalin antiserum and gave values of the same order as the radioreceptor assay. Digestion with trypsin also yielded peptides which were immunoreactive using C-terminal specific enkephalin antibody. These results, that an immunoreactive peptide is significantly increased after trypsin digestion of peaks I–IV, are in accord with those obtained with the radioreceptor assay. They indicate that an active peptide is released from a larger peptide by the trypsin digestion and that the larger peptides are not themselves active.

The receptor activities for peaks I and II were detectable only when the material of these peaks was digested with trypsin prior to assay. In addition receptor activities for peaks III and IV were greatly increased after trypsin treatment. Extracts from chromaffin cells grown in primary culture showed the same pattern of peaks as BAM when chromatographed by conventional means on Sephadex G-75 gel filtration. Furthermore chromatography of BAM or CG on Sephadex G-75 separates the enkephalin-containing polypeptides into the same pattern as that of Sephadex G-100.

Fractions corresponding to peak II and peak III from the Sephadex G-100 or G-75 gel filtration column were respectively pooled and each of the resulting pooled materials was further purified by chromatography on a Lichrosorb RP-18 HPLC column conventionally, such as for example pumping the pooled material directly onto a 10 µm, 4.6×250 mm column and eluting using a linear 0–20% 1-propanol gradient in 0.5 M formic acid/0.4 M pyridine at pH 4.0 at a flow rate of about 30 ml/hour—Lewis, R. V. et al., Int'l J. Peptide Protein Res. 13, 493 (1979); or preferably such as in accordance with the method of Kimura, S., Et al., Proc. Nat. Acad. Sci. U.S.A., 77, 1681–1685 (1980) or Lewis et. al., Proc. Nat. Acad. Sci. U.S.A., 77 5018 (1980). The pooled material corresponding to peak II was treated with an additional HPLC step on a Spherisorb CN column conventionally as for example in accordance with the method described in Lewis, R. V., et al., Anal. Biochem, 104, 153–159 (1980). Column fractions from the various chromatographic columns were monitored conventionally as by a fluorescamine detection system as described in Bohlen, P., et al., Anal. Biochem. 67, 438–445 (1975).

These chromatographic processes provided two major peptide components from Peak II designated 14 k and 11 k, having molecular weights of approximately 14 kilodaltons and 11 kilodaltons, respectively, and being purified to homogeneity. These chromatographic processes provided one major peptide component from peak III designated 8 k, having a molecular weight of approximately 8 kilodaltons and being purified to homogeneity. The amino acid analyses of 14 k, 11 k and 8 k are shown in Table II. As determined by conventional means, the partial N-terminal sequence of 11 k is -Ala-Glu-Glu-Asp$^5$-Asp-Gly-Leu, and the partial N-terminal sequence of 8 k is -Glu-Cys-Ser-Gln-Asp$^5$-Cys-Ala-Thr-Cys-Ser$^{10}$-Tyr-Arg-Leu-Ala-Arg$^{15}$. Two major active tryptic fragments of 14 k obtained by conventional trypsin digestion of 14 k were also purified by HPLC conventionally and shown to have the amino acid compositions of Met$^5$-enkephalin and Arg$^6$-Met$^5$-enkephalin.

Bovine adrenal medulla mRNA obtained by conventional methods and used to prepare in a conventional manner cDNA, which was then cloned and screened with a synthetic probe corresponding to a portion of Peptide E. After amplification of a positive clone and extraction of the DNA insert, the proenkephalin sequence was determined. The complete sequences of the 14 k, 11 k and 8 k polypeptides were deduced from the proenkephalin sequence.

Fractions corresponding to peak IV from the Sephadex G-100 or G-75 gel filtration column were pooled and further purified by chromatography on a Lichrosorb RP-18 HPLC column in accordance with any conventional method, for example, such as described earlier for a Lichrosorb RP18 HPLC column.

The fractions obtained after applying peak IV to the Lichrosorb RP-18 HPLC column show a complex pattern of peptides with at least six peptides, designated A-B, C-D, E, F-G, H-I and J (as shown in FIG. I) having opioid activity or having such activity after tryptic digestion. All of the fractions from the Lichrosorb RP-18 HPLC column, except fraction C-D, showed much greater opioid activity after trypsin digestion. The various fractions containing separately the designated peptides were further chromatographed on a Lichrosorb RP-18 (designated C$_{18}$), an ultrasphere octyl (designated C$_8$), or a Spherisorb CN (designated CN) column (in accordance with any art recognized procedure) as shown in the scheme of FIG. I. This latter process resolved the six peptides obtained from the initial Lichrosorb RP-18 HPLC column procedure into ten distinct active peptides desginated A–J (FIG. I).

The rlative proportions of the peptides A–J were found to vary from preparations to preparation, but peptides B,E,F and I were usually the major peptides present.

FIG. I shows schematically the peptides present in peak IV originally obtaned by Sephadex G-100 or G-75 gel filtration and as further chromatographed to yield peptides A–J. The percentages and nanomoles per gram for A–J represent the total opioid activity in peak IV.

FIG. I

| | | | % of Total PEAK IV | n moles/ g | molecular weight |
|---|---|---|---|---|---|
| Peak IV RP-18 | A-B C$_{18}$ | A | 9.5 | 0.78 | — |
| | | B | 12.3 | 1.02 | 3,600 |
| | C-D C$_8$ | C | 2.4 | 0.20 | — |
| | | D | 6.5 | 0.53 | — |
| | E CN | E | 14.1 | 1.17 | 3,200 |
| | F-G CN | F | 25.7 | 2.12 | 3,800 |
| | | G | 2.8 | 0.23 | — |
| | H-I CN | H | 7.3 | 0.60 | — |
| | | I | 17.2 | 1.42 | 4,900 |
| | J CN | J | 2.2 | 0.18 | — |

ANALYSIS OF PEPTIDE-B

Peptide B is a 3.6 kDal polypeptide which yielded a single tryptic peptide with opiate receptor binding activity, chromatographically identical to authentic [Met] enkephalin-Arg$^6$ and having the same amino acid composition. The finding of a [Met] enkephalin-Arg$^6$ sequence in the 3.6 kDal polypeptide indicated that the enkephalin sequence is not the carboxyl terminus. The tryptic digest also yielded free arginine and phenylalanine in approximately equimolar amounts. The 3.6 kDal polypeptide was also subjected conventionally to carboxypeptidase Y time course hydrolysis which established the carboxyl-terminal amino acid sequence as -Gly-Phe-Met-Arg-Phe-COOH. These findings indicate that the 3.6 kDal enkephalin-containing polypeptide contains a [Met] enkephalin-Arg$^6$ sequence near the carboxyl-terminal end of the molecule and that the hexapeptide is followed by phenylalanine. On the basis of the amino acid composition as shown in Table II (i.e., 2 Arg and 2 Lys) and the release of free arginine by trypsin, the [Met] enkephalin-Arg$^6$-Phe$^7$ sequence was determined to be preceded by Lys-Arg. When the amino-terminal amino acid sequence of this polypeptide was determined conventionally with automated Edman degradation, unambiguous results were obtained for the first 11 cycles. Based on all the above data, a partial sequence for the 3.6 kDal enkephalin-containing polypeptide was deduced.

ANALYSIS OF PEPTIDES F AND I

Amino acid analyses of the peptides F and I are shown in Table II. Molecular weights of about 4000 and 5000 for peptides F and I, respectively, were calculated from these analyses. These molecular weights are in accord with their elution positions on gel chromatography. Their compositions indicate that peptides F and I are distinct entities and that neither has any relationship to β-endorphin nor to α-neo-endorphin (Table II). End group analysis conventionally as by the dansyl method revealed a single amino acid for each of the peptides, thereby confirming their homogeneity. The amino terminus of peptide F is Tyr and that of peptide I is Ser.

For further chracterization, peptides F and I were each treated with trypsin and the tryptic peptides were separated by chromatography on an Ultrasphere Octyl column. Two peaks with opiate receptor binding activity were obtained in the digest of peptide F, designated F-T-1 and F-T-2 according to their order of elution. The most active tryptic peptide was F-T-2 which was chromatographically identical to authentic Met-enkephalin. The other tryptic peptide (F-T-1) eluted at a position preceding synthetic Met-enkephalin-(Arg$^6$) and coincided with synthetic Met-enkephalin-(Lys$^6$).

As shown in Table III the amino acid composition of F-T-2 was identical to that of Met-enkaphalin. F-T-1 had the same amino acid composition as Met-enkephalin-(Lys$^6$). Based on amino acid analyses equimolar amounts of both tryptic peptides, Met-enkephalin and Met-enkephalin-(Lys$^6$), were derived from peptide F. Partial sequence analysis of peptide F yielded Tyr$^1$-Gly$^2$-Gly$^3$-Phe$^4$. On the basis of all the above data, the 34 residue peptide F must contain two copies of the Met-enkephalin sequence. One is located at the amino-terminus followed by Lys, and yielding Met-enkephalin-(Lys$^6$) on digestion with trypsin. The other is at the carboxy-terminus preceded by Lys or Arg, and yielding free Met-enkephalin on digestion with trypsin.

In the case of peptdie I, only one tryptic peptide with opiate receptor binding activity, designated I-T-2, was found. This peptide was chromatographically identical to authentic Leu-Enkephalin. The amino acid composition of I-T-2 is also the same as synthetic Leu-enkephalin (Table III). Although no additional active peptides were detected in the tryptic digests, a peak (I-T-1), eluting in the same position as Met-enkephalin-(Arg$^6$), was observed. The amino acid analysis of I-T-1 was also the same as Met-enkephalin-(Arg$^6$) (Table III). Both the tryptic peptide, I-T-1 and synthetic Met-enkephalin-(Arg$^6$) were subsequently shown to be active in the radioreceptor assay at high concentrations. All the above data indicate that the 39 residue peptide I contains a Leu-enkephalin sequence, which is located at the carboxy terminus and is preceded by Lys or Arg, and a Met-enkephalin sequence in the internal portion of the peptide preceded by Lys or Arg and followed by Arg.

The amino acid sequence of peptides F and I were determined conventionally with automated Edman degradation.

Although amino acid analyses showed equal amount of the tryptic peptides Met-enkephalin and Met-enkephalin-(Lys$^6$) in peptide F, the radioreceptor binding activity of the two tryptic fragments were clearly different. The binding curves of the two tryptic peptides showed that Met-enkephalin-(Lys$^6$) binds only 9% as well to the receptor as does Met-enkephalin. Intact peptide F, which has a Met-enkephalin-(Lys$^6$) sequence at its amino terminus, showed a binding activity similar to that of synthetic Met-enkephalin-(Lys$^6$). The binding curve for the unfractionated tryptic digest of peptide I was almost identical to that of synthetic Leu-enkephalin. Met-enkephalin-(Arg$^6$) binds very poorly to the receptor and thus contributes very little to the activity of the tryptic digest of peptide I. This hexapeptide, as well as intact Peptide I, exhibited less than 3% of the binding activity of Leu-enkephalin.

Radioimmunoassay with an amino-terminal directed Met-enkephalin antiserum showed that intact peptide F does crossreact and that there is a significant increase, about 1.4 fold, in crossreactivity after trypsin digestion. Intact peptide I showed crossreactivity with the above antiserum only after trypsin digestion. Both intact peptides F and I showed about 0.1% crossreactivity towards a carboxy-terminal directed Leu-enkephalin antiserum. However, after trypsin digestion, the crossreactivity of peptide I increased to 100%, whereas the crossreactivity of peptide F was unchanged. None of the ten peptides in Peak IV exhibited crossreactivity with an antiserum to $\beta$-endorphin. Unfractionated chromaffin granule extracts were also negative to a radioimmunoassay for ACTH.

ANALYSIS OF PEPTIDE E

Tryptic Digestion of Peptide E provided by conventional Lichrosorb RP-18, 5 column, using a linear concentration gradient of 0 to 20% N-propanol in 210 minutes at a flow rate of 20 ml/hr, three major tryptic peptides designated E-T-1, E-T-2 and E-T-3 (Table III).

Amino acid compositions and tryptic digestions of peptide-E shows that its amino acid sequence corresponds to amino acid residues 15–39 of known peptide-I. The chemical data and sequence, as determined conventionally by automated Edman degradation, of peptide-E indicates that peptide-E is related to peptide-I. This relationship is surprising and unexpected in that peptide-E does not appear to be related to $\beta$-endorphin which has, except for a Met-enkephalin group, an amino acid sequence substantially different from peptide-E and is pharmaceutically acceptable and useful as an opiate antagonist.

TABLE II

| | AMINO ACID COMPOSITION OF ADRENAL PEPTIDES | | | | | | | | |
|---|---|---|---|---|---|---|---|---|---|
| | B | E | F | I | 14k | 11k | 8k | $\beta$-Endorphin | $\alpha$-Neo-Endorphin |
| Asx | | 1 | 2 | 2 | 7 | 15 | 4 | 2 | 0 |
| Thr | | 0 | 0 | 1 | 7 | 0 | 5 | 3 | 0 |
| Ser | | 0 | 0 | 1 | 6 | 8 | 4 | 2 | 0 |
| Glx | | 2 | 6 | 6 | 19 | 17 | 9 | 3 | 0 |
| Pro | | 1 | 1 | 4 | 7 | 0 | 7 | 1 | 1 |
| Gly | | 5 | 6 | 5 | 10 | 17 | 3 | 3 | 3 |
| Ala | | 0 | 1 | 0 | 7 | 6 | 6 | 2 | 0 |
| CySH | | 0 | 0 | 0 | 6 | 0 | 6 | 0 | 0 |
| Val | | 1 | 2 | 1 | 2 | 2 | 0 | 1 | 0 |
| Met | | 2 | 3 | 2 | 5 | 2 | 1 | 1 | 0 |
| Ile | | 0 | 0 | 0 | 0 | 0 | 0 | 2 | 0 |
| Leu | | 1 | 3 | 3 | 18 | 14 | 15 | 2 | 1 |
| Tyr | | 3 | 3 | 3 | 5 | 2 | 2 | 1 | 3 |
| Phe | | 2 | 2 | 2 | 3 | 2 | 1 | 2 | 1 |
| His | | 0 | 0 | 1 | 1 | 2 | 1 | 1 | 0 |
| Lys | | 1 | 3 | 3 | 11 | 5 | 6 | 5 | 2 |
| Arg | | 4 | 1 | 5 | 4 | 6 | 2 | 0 | 4 |
| Cys | | | | | 0 | | 4 | | |

TABLE II-continued

| | | | | AMINO ACID COMPOSITION OF ADRENAL PEPTIDES | | | | |
|---|---|---|---|---|---|---|---|---|
| | B | E | F | I  14k | 11k | 8k | β-Endorphin | α-Neo-Endorphin |
| Trp | 2 | 0 | 0 | — | 1 | 1 | 0 | 0 |
| | 25 | 33 | 39 | 118 | 99 | 73 | 31 | 15 |
| Molecular Weight | | | | 14,000 | 11,000 | 8,000 | | |

TABLE III

AMINO ACID COMPOSITION OF OPIOID ACTIVE TRYPTIC PEPTIDES FROM PEPTIDEE E, F AND I

| AMINO ACID RESIDUES | E-T-1 | E-T-2 | E-T-3 | F-T-1 | F-T-2 | I-T-1 | I-T-2 |
|---|---|---|---|---|---|---|---|
| Asx | 0 | 1 | 0 | 0 | 0 | 0 | 0 |
| Thr | 0 | 0 | 0 | 0 | 0 | 0 | 0 |
| Ser | 0 | 0 | 0 | 0 | 0 | 0 | 0 |
| Glx | 0 | 2 | 0 | 0 | 0 | 0 | 0 |
| Pro | N.D. | N.D. | N.D. | 0 | 0 | 0 | 0 |
| Gly | 2 | 1 | 2 | 2 | 2 | 2 | 2 |
| Ala | 0 | 0 | 0 | 0 | 0 | 0 | 0 |
| Val | 0 | 1 | 0 | 0 | 0 | 0 | 0 |
| Met | 1 | 2 | 0 | 1 | 1 | 1 | 0 |
| Ile | 0 | 0 | 0 | 0 | 0 | 0 | 0 |
| Leu | 0 | 0 | 1 | 0 | 0 | 0 | 1 |
| Tyr | 1 | 1 | 1 | 1 | 1 | 1 | 1 |
| Phe | 1 | 0 | 1 | 1 | 1 | 1 | 1 |
| His | 0 | 0 | 0 | 0 | 0 | 0 | 0 |
| Lys | 0 | 1 | 0 | 1 | 0 | 0 | 0 |
| Arg | 1 | 1 | 0 | 0 | 0 | 1 | 0 |
| Trp | 0 | 2 | 0 | | | | |
| Cys | 0 | 0 | 0 | 0 | 0 | 0 | 0 |
| N-terminal | | | | Tyr | Tyr | Tyr | Tyr |

Peak V from Sephadex G-100 was chromatographed conventionally on Lichrosorb RP-18 column [such as 10 μm, 4.6×250 mm column, using a step gradient of 0% (5 min), 5% (5 min), 10% (25 min), 15% (30 min) and 40% (15 min) 1-propanol in 0.5 M formic acid-0.4 M pyridine (pH 4.0) with a flow rate of 35 ml/hr]. Aliquots (20 μl) of fractions (3 min) were assayed with the radioreceptor assay. Peak V was composed of several peptides which were equally active with or without trypsin digestion. Chromatography on RP-18 revealed opioid activity in the calibrated Met- and Leu-enkephalin positions and also in two regions before the elution position of Met-enkephalin in fractions 6 and 7 and one region after the elution position of Leu-enkephalin (fractin 16). [A similar chromatographic pattern was obtained from bovine striatal extracts although the relative amounts of these additional peptides differed].

The peptide eluting in the Leu-enkephalin position was purified to homogeneity by further chromatography on RP-18. It was shown to have the amino acid composition Tyr [1], Gly[2], Phe[1], and Leu[1].

In order to determine whether fractions 6,7, and 16 were indeed separate entities differing chromatographically from the enkephalins, these fractions were lyophilized, redissolved and rechromatographed. Each opioid peptide eluted at its original position. These three fractions (6,7, and 16) were characterized by comparing their activity in the radioreceptor assay and the N- and C-terminal directed enkephalin radioimmunoassays (as shown in Table IV). All the fractions interacted well with the N-terminal specific antiserum. None of the three fractions interacted very well with the C-terminal directed antiserum.

TABLE IV

Radioreceptor Assay and Radioimmunoassay of Fractions, 6, 7 and 16 from RP-18

| Fraction | Radioreceptor | N-Terminal | C-Terminal |
|---|---|---|---|
| 6 | 1.1 | 0.8 | <0.01 |
| 7 | 1.4 | 1.2 | 0.03 |
| 16 | 1.3 | 1.2 | 0.06 |
| Met-enk (std) | 1.0 | 1.0 | 0.03 |
| Leu-enk (std) | 1.0 | 0.4 | 1.0 |

[1]These values are for 1.3 g wet weight of chromaffin granules isolated from 30 g of adrenal medulla and are expressed in nmoles/fraction.

Fraction 16 from peak V has been purified conventionally by isocratic elution from RP-18. Its amino acid compositon was found to by Tyr(1), Gly(2), Phe(2), Met(1), Arg(1). When the peptide was digested with trypsin the active fragment coeluted with $Arg^6$-Met enkephalin indicating this peptide has a C-terminal of Arg-Phe, giving the structure: Tyr-Gly-Gly-Phe-Met-Arg-Phe.

Radioimmunoassays were performed using a C-terminal directed Leu-enkephalin antibody and a N-terminal directed Met-enkephalin antibody. The characteristics of these antibodies and methods of use have been described previously and were followed in Lewis, R. V., et al., Biochem. Biophys. Res. Commun. 89, 822 (1979).

Amino Acid analysis of enkephalin-containing polypeptides of this invention were performed conventionally as by the procedure of Stein S., et al., ABB 155, 203–212 (1973). For example 100 pmole of the polypeptide samples were hydrolyzed at 110° C. for 22 hours in 200 μl of constant boiling hydrochloric acid containing 0.1% thioglycolic acid. Tryptophan was determined by hydrolyzing in the presence of 4% (v/v) thioglycolic acid. Amino acid analysis was performed at the picomole level with a fluorescamine amino acid analyzer.

Tryptic digestion of the enkephalin-containing polypeptides of this invention were performed by dissolving approximately 2 n moles of the polypeptide in 200 μl of 0.1 M sodium phosphate buffer (pH 8.2) and adding TPCK-trypsin (2 μg) at 37° C. for 18 hours. Analysis of an aliquot of the resulting digested mixture was by o-phthaldialdehyde derivatization followed by reverse-phase HPLC according to the method of Lindroth and Hopper, Anal. Chem. 51, 1667 (1979). The digest mixture was then purified conventionally on a Lichrosorb RP-18 column using a linear concentration gradient of 0 to 20% by volume of n-propanol.

Aliquots of the column effluents were lyophilized and assayed for opiate receptor binding activity. The elution profile of the tryptic peptides thus obtained was compared to a standard composing Met-enkephalin-(Lys[6]), Met-enkephalin-(Arg[6]), Met-enkephalin, Leu-enkephalin, Met-enkephalin-(Arg[6]-Phe[7]) and eluted under similar conditions from a similar ultrasphere octyl column.

Preparation of synthetic Tyr-Gly-Gly-Phe-Met-Arg-Phe was as follows: 2 g (1.0 mM) of tert-butyloxycarbonyl [BOC]-Phe resin was prepared from chloromethyl-polystyrene and Boc-Phe by the art recognized cesium salt method. To the Boc-Phe resin was coupled 1.4 g of Amyloxycarbonyl[AOC]-Arg(TOS), 0.75 g of Boc-Met, 0.8 g Boc-Phe, 0.53 g Boc-Gly in two couplings, and 1.5 g of Boc-Tyr-p-bromobenzyloxycarbonyl. The sequence of steps in each cycle was washed three times with methylene chloride (MC); 40% Trifluoroacetic acid/MC (consisting of a one minute pre wash and a 20 minute deprotection step); a wash with MC; a wash with ethanol, wash three times with MC; and 2 minutes wash with a ten minute neutralization time with 10% triethylamine; followed by three washed MC. The Boc-amino acid and dicyclohexylcarbodimide were added in MC and stirred for two hours. If the resin showed complete coupling by the Kaiser test, the next cycle was begun. After the last addition, the resulting peptideresin was washed with MC and ethanol after deprotection and dried. The peptide was removed from the resin by treatment with hydrogen fluoride for one hour at 0° C. Dimethylsufide (0.5 ml) and anisole (6 ml) were added for protection. After evacuation, the peptide was washed with ether, dissolved in 20% acetic acid and lyophilized.

The enkephalin-containing polypeptides of this invention are effective opiate agonist which can be seen by their effect on the guinea pig ileum as determined by the well established art recognized methods. The guinea pig ileum myenteric plexus longitudinal muscle preparation is a classic in vitro system for studying the effects of opiates [Kosterlitz, H. W. and Waterfiled, A. D. (1975) Ann. Rev. Phamacol. 15, 2947; Schulz, R. and Goldstein, A. (1973) Br. J. Pharmacol. 48, 655–666]. Opiates and opioid peptides inhibit electrically-stimlated contractions of this preparation. These effects are reversed by the opiate agonist naloxone. Peptide E is 20–30 times more potent than the pentapeptide [Met]-enkephalin, with an $IC_{50}$ of 1–2 nM. This high potency is also reflected in the slow rate of recovery from inhibition after washing out the peptide. Comparison with another potent opioid peptide, dynorphin A. Goldstein, et al., Proc. Nat'l Acad. Sci. U.S.A. 76, 6666 (1979), showed Peptide E to be almost as potent. That the effects of the polypeptides of this invention are mediated by opiate receptors is indicated by the reversal of inhibition by naloxone in test animals as shown by comparing its biological activity with β-endorphin in test animals.

For the analgesic assay, mice were injected (intracerebral ventrical) with 6 n moles of the synthetic peptide (Tyr-Gly-Gly-Phe-Met-Arg-Phe). The tail flick response assay was carried out according to the method of Dayton, et al., Proc. Soc. Exp. Biol. Med. 142; 1011 (1973). The tail flick response (analgesic activity) was measured prior to injection and at 2,5 and 10 minutes post injection time. Results are tabulated in Table V. Further results are given in Inturris, et. al., Proc. Nat'l. Acad. Sci. (U.S.A.), 77,5512 (1980).

TABLE V

| No. of Mice Responsive/ Total No. of Mice | Injection Material | Dose | Volume | Prior Injection Time (Control) Predose | Post Injection Time | | | | Response |
|---|---|---|---|---|---|---|---|---|---|
| | | | | | 2 min. | 5 | 10 | 20 | |
| 0/3 | Saline | | 10 | 6.2 | 3.7 | | 5.6 | | Neg. |
| " | | | | 4.5 | 5.0 | | 5.8 | | Neg. |
| " | | — | | 5.0 | 4.3 | | 5.6 | | Neg. |
| " | Met Enk | 120nm | 10nl. | 4.1 | 4.0 | | 6.3 | | Neg. |
| " | | | | 5.4 | 4.7 | | 5.9 | | Neg. |
| " | | | | 4.6 | 4.0 | | 5.0 | | Neg. |
| 3/3 | Acetylcholine | 20ng | 10nl | 4.6 | | 6.1 | >10 | | Pos. |
| " | | | | 5.0 | | >10 | | | Pos. |
| " | | | | 4.5 | | >10 | >10 | | Pos. |
| " | Beta-endorphin | 4.5nm | 5nl | 4.0 | 5.9 | >10 | | >10 | Pos. |
| " | | | | 4.7 | 3.0 | >10 | | >10 | Pos. |
| " | | | | 4.2 | 4.4 | >9 | | >10 | Pos. |
| 5/7 | | | | 5.4 | 3.8 | | 8 | Neg. | |
| " | | | | 4.4 | | 3.4 | >10 | | Pos. |
| " | | | | 4.0 | | 3.4 | 3.8 | | Neg. |
| " | | | | 4.3 | | 3.1 | | >10 | Pos. |
| 1/6 | Phosphate-Saline | | 10nl | 3.5 | | 4.5 | 4.4 | | Neg. |
| " | | | | 4.2 | 3.2 | | >10 | | Pos. |
| " | | | | 4.2 | | 3.5 | 3.9 | | Neg. |
| " | | | | 4.9 | | 6.0 | | 4.0 | Neg. |
| " | | | | 4.3 | 5.0 | 5.6 | | 8.0 | Neg. |
| " | | | | 4.2 | 5.5 | 4.8 | | 5.0 | Neg. |
| 4/8 | Arg[6]—Phe[7] met-enkephalin | 10nl | 5.7 | 4.9 | | 6.3 | Neg. | | |
| " | | | | 5.2 | 4.6 | | 5.8 | | Neg. |
| " | | | 5nl | 4.6 | 4.3 | 5.4 | >10 | | Pos. |
| " | | | | 3.6 | 4.0 | 4.2 | >10 | | Pos. |
| " | | | | 3.7 | 3.4 | 3.8 | 5.0 | | Neg. |
| " | | | | 3.7 | 4.5 | 9.0 | >10 | | Pos. |

TABLE V-continued

| No. of Mice Responsive/ Total No. of Mice | Injection Material | Dose | Volume | Prior Injection Time (Control) Predose | Post Injection Time 2 min. | 5 | 10 | 20 | Response |
|---|---|---|---|---|---|---|---|---|---|
| " | | | | 4.0 | 4.0 | 4.0 | 4 | | neg. |

Pharmaceutically acceptable acid addition salts of the enkephalin-containing polypeptides are included in this invention and include salts formed from alkali metal e.g. sodium or potassium and acceptable base salts include salts formed from organic bases such as guanidine. Furthermore the cations of residues in peptide-E include counter ions thereto such as hydrochloride, hydrobromide, sulfate, phosphate, maleate, acetate, citrate, malate, ascorbate and the like, preferably hydrochloride.

The compounds of the present invention are potent opiate agonists and thus are useful as analgesics. In particularly they can be used as medicaments in the form of pharmaceutical preparations prepared in conventional manner and having direct or delayed liberation of the active ingredient in association with a compatible carrier material. This carrier material can be an organic or inorganic inert carrier material suitable for enteral, precutaneous or parenteral application such as water, gelatin, gum arabic, lactose, starch, magnesium stearate, talc, vegetable oils, polyalkylene-glycols, petroleum jelly, etc. The pharmaceutical preparations can be made up in a solid form (e.g. as tablets, dragees, suppositories or capsules) or in a liquid form (e.g. as solutions, suspensions or emulsions). A preferred form suitable for parenteral administration involves preparation of a purified, lyophilized form of the active compound which is reconstituted prior to use by the addition of sterile, distilled water or saline.

If necessary, the pharmaceutical preparations can be sterilized and/or contain adjuvant substances such as preserving, stabilizing, wetting or emulsifying agents, salts for the variation of the osmotic pressure or substances acting as buffers.

The compounds of the present invention can be conveniently administered to warm-blooded mammals by the parenteral route, preferably intravenously, in any pharmaceutically effective amount conveniently and conventionally determined by anyone skilled in the art. The effective amount administered, of course, may vary depending on the severity of the condition being treated and the duration of the treatment. A convenient dosage form is a pharmaceutical preparation containing 0.1 mg to 50 mg of the active ingredient, e.g. a compound of the invention, per kg of body weight per administration, with a dosage in the range of about 1 mg to 50 mg per administration preferred.

What is claimed is:

1. A peptide compound endogenous in mammalian adrenal glands, essentially free of other endogenous peptides and having the following amino acid sequence:

```
                5                          10
Glu—Cys—Ser—Gln—Asp—Cys—Ala—Thr—Cys—Ser—
       15                         20
—Tyr—Arg—Leu—Ala—Arg—Pro—Thr—Asp—Leu—Asp—
       25                         30
—Pro—Leu—Ala—Cys—Thr—Leu—Glu—Cys—Glu—Gly—
       35                         40
—Lys—Leu—Pro—Ser—Leu—Arg—Thr—Trp—Glu—Thr—
       45                         50
—Cys—Lys—Glu—Leu—Leu—Gln—Leu—Thr—Lys—Leu—
       55                         60
—Glu—Leu—Pro—Pro—Asp—Ala—Thr—Ser—Ala—Leu—
       65                         70
—Ser—Lys—Gln—Glu—Glu—Ser—His—Leu—Leu—Ala—
       75                         80
—Lys—Lys—Tyr—Gly—Gly—Phe—Met—Lys—Arg—Tyr—
       85                         90
—Gly—Gly—Phe—Met—Lys—Lys—Met—Asp—Glu—Leu—
       95                         100
—Tyr—Pro—Leu—Glu—Val—Glu—Glu—Glu—Ala—Asn—
       105                        110
—Gly—Gly—Glu—Val—Leu—Gly—Lys—Arg—Tyr—Gly—
                                    —Gly—Phe—Met
``` and the pharmaceutically acceptable acid addition salts or base salts thereof.

2. A peptide compound endogenous in mammalian adrenal glands, essentially free of other endogenous peptides and having the following acid sequence:

```
                5                          10
Asp—Ala—Glu—Glu—Asp—Asp—Gly—Leu—Gly—Asn—
       15                         20
—Ser—Ser—Asn—Leu—Leu—Lys—Glu—Leu—Leu—Gly—
       25                         30
—Ala—Gly—Asp—Gln—Arg—Glu—Gly—Ser—Leu—His—
       35                         40
—Gln—Glu—Gly—Ser—Asp—Ala—Glu—Asp—Val—Ser—
       45                         50
—Lys—Arg—Tyr—Gly—Gly—Phe—Met—Arg—Gly—Leu
``` and the pharmaceutically acceptable acid addition salts or base salts thereof.

3. A peptide compound endogenous in mammalian adrenal glands, essentially free of other endogenous peptides and having the following amino acid sequence:

```
                5                          10
Glu—Cys—Ser—Gln—Asp—Cys—Ala—Thr—Cys—Ser—Tyr—
       15                         20
Arg—Leu—Ala—Arg—Pro—Thr—Asp—Leu—Asp—Pro—Leu—
       25                         30
Ala—Cys—Thr—Leu—Glu—Cys—Glu—Gly—Lys—Leu—Pro—
       35                         40
Ser—Leu—Arg—Thr—Trp—Glu—Thr—Cys—Lys—Glu—Leu—
       45                 50                 55
Leu—Gln—Leu—Thr—Lys—Leu—Glu—Leu—Pro—Pro—Asp—
                         60                 65
Ala—Thr—Ser—Ala—Leu—Ser—Lys—Gln—Glu—Glu—Ser—
                70                 75
His—Leu—Leu—Ala—Lys—Lys—Tyr—Gly—Gly—Phe—Met
``` and the pharmaceutically acceptable acid addition salts or base salts thereof.

4. A peptide compound endogenous in mammalian adrenal glands, essentially free of other endogenous peptides and having the following amino acid sequence:

```
   1               5                    10
Tyr—Gly—Gly—Phe—Met—Arg—Arg—Val—Gly—Arg—Pro—
          15                  20
Glu—Trp—Trp—Met—Asp—Tyr—Gln—Lys—Arg—Tyr—Gly—
                                      Gly—Phe—Leu
``` and the pharmaceutically acceptable acid addition salts or base salts thereof.

5. A peptide compound endogenous in mammalian adrenal glands, essentially free of other endogenous peptides and having the following amino acid sequence:

```
   1                  5                      10
Phe—Ala—Glu—Pro—Leu—Pro—Ser—Glu—Glu—Glu—Gly—
         15                  20
Glu—Ser—Tyr—Ser—Lys—Glu—Val—ProGlu—Met—Gly—
              25                  30
       Lys—Arg—Tyr—Gly—Gly—Phe—Met—Arg—Phe
``` and the pharmaceutically acceptable salts or base salts thereof.

6. A peptide compound endogenous in mammalian adrenal glands, essentially free of other endogenous peptides and having the following amino acid sequences:

```
   1              5                      10
Tyr—Gly—Gly—Phe—Met—Lys—Lys—Met—Asp—Glu—Leu—
              15                   20
Tyr—Pro—Leu—Glu—Val—Glu—Glu—Glu—Ala—Asn—Gly—
                 25                      30
       Gly—Glu—Val—Leu—Pro—Leu—Gly—Lys—Arg—Tyr—
                                         34
                         Gly—Gly—Phe—Met
``` and the pharmaceutically acceptable acid addition salts or base thereof.

7. A peptide compound endogenous in mammalian adrenal glands, essentially free of other endogenous peptides and having the following amino acid sequence:

```
   1                 5                     10
Ser—Pro—His—Leu—Glu—Asp—Glu—Thr—Lys—Glu—Leu—
             15                      20
Gln—Lys—Arg—Tyr—Gly—Gly—Phe—Met—Arg—Arg—Val—
            25                        30
Gly—Arg—Pro—Glu—Trp—Trp—Met—Asp—Tyr—Gln—Lys—
                     35                  39
                Arg—Tyr—Gly—Gly—Phe—Leu
``` and the pharmaceutically acceptable acid addition salts or base salts thereof.

* * * * *